(12) United States Patent
Mentzel et al.

(10) Patent No.: US 9,551,736 B2
(45) Date of Patent: Jan. 24, 2017

(54) CONTACT-INDEPENDENT ELECTRICAL CONDUCTANCE MEASUREMENT

(75) Inventors: Tamar S. Mentzel, Fair Lawn, NJ (US); Kenneth MacLean, Hingham, MA (US); Marc A. Kastner, Newton, MA (US); Nirat Ray, Natick, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1093 days.

(21) Appl. No.: 13/570,556

(22) Filed: Aug. 9, 2012

(65) Prior Publication Data
US 2015/0260769 A1    Sep. 17, 2015

Related U.S. Application Data (60) Provisional application No. 61/522,778, filed on Aug. 12, 2011.

(51) Int. Cl.
*G01R 27/16*    (2006.01)
*G01N 27/414*   (2006.01)
*G01R 19/00*    (2006.01)

(52) U.S. Cl.
CPC .......... *G01R 27/16* (2013.01); *G01N 27/4146* (2013.01); *G01R 19/0092* (2013.01)

(58) Field of Classification Search
CPC .. G01R 27/16; G01R 19/0092; G01N 27/4146
See application file for complete search history.

(56) References Cited

U.S. PATENT DOCUMENTS

| | | |
|---|---|---|
| 6,498,360 B1 | 12/2002 | Jain et al. |
| 2010/0156475 A1 | 6/2010 | Simin et al. |
| 2014/0247067 A1* | 9/2014 | He ............... G01R 31/2621 324/762.09 |

OTHER PUBLICATIONS

PCT/US2012/050083, International Search Report, First sheet, Second sheet, and patent family annex, Mar. 2013.
PCT/US2012/050083, Written Opinion of the International Searching Authority, Form PCT/ISA/237 cover Sheet, Box I sheet, Box V sheet, and Box V supplemental Sheets Feb. 1-3, 2014.

(Continued)

*Primary Examiner* — Jermele M Hollington
(74) *Attorney, Agent, or Firm* — Theresa A. Lober (57) ABSTRACT

Electrical conductance measurement system including a one-dimensional semiconducting channel, with electrical conductance sensitive to electrostatic fluctuations, in a circuit for measuring channel electrical current. An electrically-conductive element is disposed at a location at which the element is capacitively coupled to the channel; a midpoint of the element aligned with about a midpoint of the channel, and connected to first and second electrically-conductive contact pads that are together in a circuit connected to apply a changing voltage across the element. The electrically-conductive contact pads are laterally spaced from the midpoint of the element by a distance of at least about three times a screening length of the element, given in SI units as $(K\epsilon_0/e^2 D(E_F))^{1/2}$, where K is the static dielectric constant, $\epsilon_0$ is the permittivity of free space, e is electron charge, and $D(E_F)$ is the density of states at the Fermi energy for the element.

13 Claims, 8 Drawing Sheets

(56) References Cited

OTHER PUBLICATIONS

Mentzel et al., "Contactless measurements of electrical conductance of a thin film amorphous germanium," Mesoscale and Nanoscale Physics, Materials Science, arXiv:1006.5948, pp. 1-8, Oct. 2010.
MacLean et al., "The Effect of Electrostatic Screening on a Nanometer Scale Electrometer," Nano Letters 11 (1), pp. 30-34, Dec. 2010.
MacLean et al., "Measuring Charge Transport in a Thin Solid Film Using Charge Sensing," Nano Letters 10 (3), pp. 1037-1040, Feb. 2010.
Mentzel et al., "Contact-Independent Measurement of Electrical Conductance of a Thin Film with a Nanoscale Sensor," Nano letters, vol. 11, pp. 4102-4106, Sep. 2011.
MacLean, "Charge Detection in Semiconductor Nanostructures," Ph.D. Thesis, Massachusetts Institute of Technology, pp. 1-145, Feb. 2010.

\* cited by examiner

CONTACT-INDEPENDENT ELECTRICAL CONDUCTANCE MEASUREMENT

CROSS-REFERENCE TO RELATED APPLICATIONS

This application claims the benefit of U.S. Provisional Application No. 61/522,778, filed Aug. 12, 2011, the entirety of which is hereby incorporated by reference.

STATEMENT REGARDING FEDERALLY SPONSORED RESEARCH

This invention was made with Government support under Contract No. DE-FG02-08ER46515, awarded by the Department of Energy; and under Contract No. W911NF-07-D-0004, awarded by the Army Research Office. The Government has certain rights in the invention.

BACKGROUND

This invention relates generally to techniques for measuring electrical conductance, and more particularly relates to the measurement of electrical conductance in thin solid state materials and structures.

The measurement of electrical conductance has become an important technique for characterizing solid state systems. For example, the examination of the dependence of the electrical resistance of a solid state system, as indicated by measured electrical conductance, on external variables such as temperature, electrical and magnetic fields, and light exposure, has enabled intimate probing of novel solid state physics effects. Beyond such analysis of particular external stimuli on a given system, electrical characterization is required in general of new materials and structures to enable their reliable implementation in a wide range of microelectronic, biological, and chemical applications.

For many microscale and nanoscale materials and structures, the measurement of electrical conductance is not straightforward. For example, effects can be introduced by electrically conducting contact pads that are located at the site of a given material or structure for making electrical contact to the material or structure under measurement. The contact resistance of such electrical contact pads, i.e., the electrical resistance of the interface between the electrically conducting material forming the contact pads and the material under measurement, as opposed to the intrinsic resistance of the material or structure under measurement, can for many configurations dominate the overall resistance of a micro-device system or other micro-scale structure, over the intrinsic resistance of a material or structure in the system that is under measurement.

As a result, contact resistance can limit the operation as well as characterization of micro-scale systems. For example, for nanometric structures, the area of electrical contact is correspondingly small, producing an increased contact resistance. Because a nanometric channel length is correspondingly short, the resistance of a nanometric channel is relatively low. As a result, as the as device sizes are reduced, contact resistance can begin to dominate the overall resistance of a nanometric field effect structure. For example, in graphene electronics, the metal-graphene interface at contact pads, and the resistance associated with this interface has limited the ability to produce high-performance graphene transistors. In organic electronics, contact pad material has been found to form a Schottky barrier with an organic material due to, e.g., damage of or penetration into the organic material, producing a resistive interface that introduces a voltage drop, irrespective of work function. As a result, the measured electrical resistance of, e.g., an organic monolayer, can vary by four orders of magnitude, depending on the choice of contact material and the method of contact with the material. Further, it is found that as charge mobility is increased in novel organic materials, contact effects and Schottky barriers become more pronounced. Schottky barriers between contact pads and a material under analysis have long been obstacles to the characterization of semiconductor films, and as novel semiconducting materials are developed, it can be difficult to discern the effect of contacts on the material measurements.

One technique for eliminating contact resistance effects from an electrical conductance measurement is a four-point probe measurement, in which separate pairs of electrical current-carrying and voltage-sensing electrodes are employed to eliminate the contribution of contact resistance to measurement of impedance. As materials and structures evolve to the nanoscale, four-point probes are found to be incompatible with electrical measurement, however. For example, four point probes can interfere with current flow, e.g., in nanoscale films, and can damage soft, organic nanoscale materials and biological structures. Conventional electrical measurement techniques are therefore found to be increasingly inadequate for characterization of microscale and nanoscale materials and systems.

SUMMARY OF THE INVENTION

An electrical conductance measurement system is provided to enable the measurement of conductance in materials and structures for which such measurement is conventionally limited. In the system, there is provided a one-dimensional semiconducting channel having an electrical conductance that is sensitive to electrostatic fluctuations in an environment of the channel. The semiconducting channel is provided in a circuit that is connected to measure electrical current through the channel. An electrically-conductive element is disposed at a location at which the element is capacitively coupled to the channel, with a midpoint of the element aligned with about a midpoint of the channel. The element is connected to a first electrically-conductive contact pad and a second electrically-conductive contact pad that are together in a circuit connected to apply a changing voltage across the element. Each of the first and second electrically-conductive contact pads are laterally spaced from the midpoint of the element by a distance of at least about three times a screening length of the element. The screening length is given in SI units as $(K\in_0/e^2 D(E_F))^{1/2}$, where K is the static dielectric constant, $\in_0$ is the permittivity of free space, e is the electron charge, and $D(E_F)$ is the density of states at the Fermi energy for the element.

The one-dimensional semiconducting channel can be provided as a field effect transistor. The field effect transistor includes an electrically-conducting gate that is disposed on an electrically-insulating surface of a substrate. The gate includes a narrowed gate region having a width corresponding to a one-dimensional inversion channel. The gate is connected to a voltage source bias providing a one-dimensional inversion channel in the substrate under the narrowed gate region. The transistor further includes a source and a drain that are together in a circuit connected to measure electrical current through the inversion channel.

With these configurations, the electrical conductance measurement system enables the electrical characterization of materials, structures, chemicals, and systems that include non-Ohmic, blocking contacts that prohibit conventional conductance measurement techniques. The system also enables the characterization of high-resistance materials and structures for which conventional measurement techniques are not applicable.

Other features and advantages will be apparent from the following description and accompanying figures, and from the claims.

DETAILED DESCRIPTION

Figure 1:
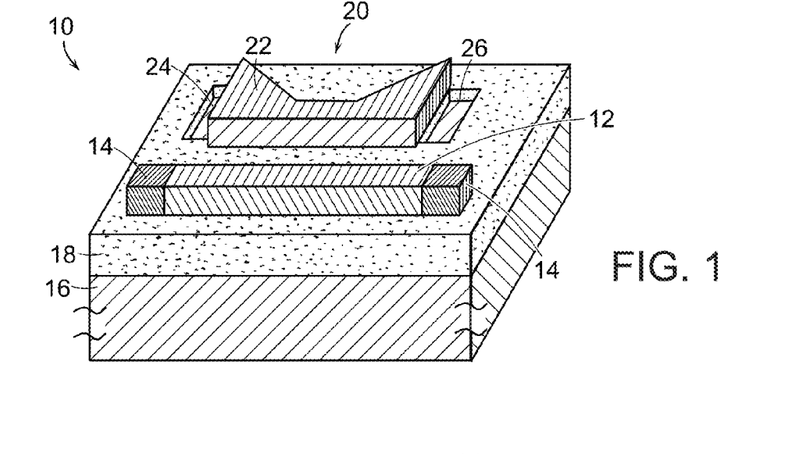
FIG. 1 is a perspective schematic view of an example contact-independent conductance measurement system.

Referring to FIG. 1, there is shown a perspective schematic view of an example system 10 configured for making a contact-independent electrical conductance measurement. The conductance measurement system 10 is configured to accommodate a solid state element 12, e.g., a material layer or film of material, a biological sample, a chemical deposit, or other substance or structure, whether three-dimensional or electromechanical in nature, for which it is desired to make a measurement of electrical conductance. The terms "solid state element" and "element" will be used herein to refer to any structure or material, whether organic or inorganic, for which a conductance measurement is to be made. The element 12 is electrically-conductive; that is, the element conducts electricity or electrical charge, to at least some degree. The element 12 under test is electrically contacted by electrically conductive contact pads 14 in any suitable manner. One contact pad is provided at each end of the element 12 or at any suitable location along the element length. These contact pads 14, along with the element under test, can be disposed on any suitable support structure, e.g., a substrate 16, which can in turn include any number of surface layers 18 or bulk configuration. The surface on which the element under test is disposed is preferably substantially electrically insulating, and therefore if the support structure 16 is electrically conducting, an electrically insulating surface layer 18 can be preferred for many applications.

The system is configured to provide, in the vicinity of the element under test 12, a one-dimensional, electrically semiconducting, sensing channel. The sensing channel is characterized by an electrical conductance that is sensitive to the electrostatic environment of the channel. The sensing channel can be provided as any suitable configuration, including, e.g., a carbon nanotube, a semiconducting nanowire, an alignment of nanocrystals, or other arrangement. For many applications, a sensing channel that can be controllably formed, e.g., by a control gate, in a material or substrate, can be convenient. FIG. 1 illustrates an example of this, with a metal-oxide-semiconductor field-effect transistor (MOSFET) 20. The MOSFET 20 includes an electrically conducting gate structure 22 adjacent to a source 24 region and a drain region 26. This MOSFET structure can be conveniently formed on, e.g., a layer 18 consisting of an electrically insulating material that is provided on, e.g., a substrate 16 that is a doped silicon substrate or other semiconductor in which dopant source and drain regions can be formed and in which an inversion channel, operating here as the sensing channel, can be formed.

The field effect transistor shown in FIG. 1 is one example of a device for producing a suitable sensing channel for use in the conductance measurement system, but is not required. Any one-dimensional semiconducting channel can be employed, and can be arranged in any suitable manner.

Figure 2:
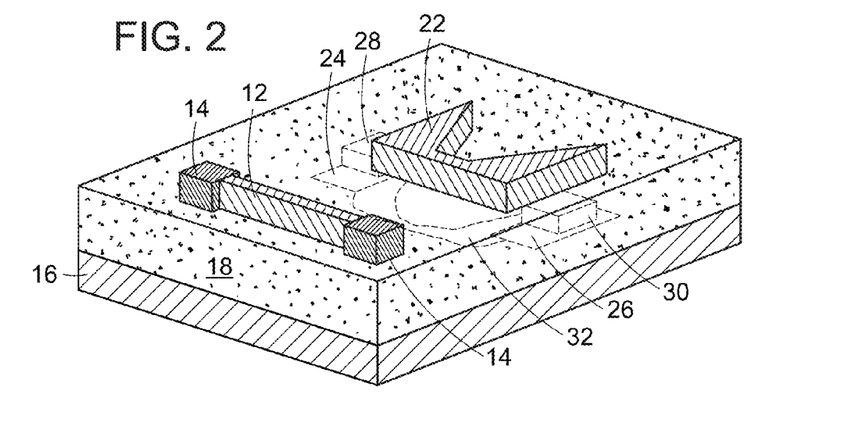
FIG. 2 is a perspective schematic view of the conductance measurement system of FIG. 1 illustrating the formation of an inversion channel during operation of the system.

Referring also to FIG. 2, considering the example of the MOSFET channel for clarity of description, in operation of the measurement system 10 in brief, the gate 22 of the MOSFET 20 is electrically biased, along with source region 24 and drain region 26 having corresponding electrical contacts 28, 30, respectively, and the element under test is electrically biased by application of a voltage across the electrical contacts 14. Under controlled biasing, as explained in detail below, a one-dimensional inversion channel of the MOSFET 20 senses charge diffusion in the element under test 12 via capacitive coupling to the element, rather than direct physical contact to the element. Preferably, at least a portion or region of the gate of the MOSFET is sufficiently narrow that the inversion channel 32 that forms in the substrate, is one-dimensional, with a conductance that varies in response to electrostatic fluctuations in the environment of the inversion channel. With the MOSFET configured nearby the element under test, the conductance of the MOSFET channel thereby varies as charge diffuses in the element. From measurements of the time dependence of the conductance of the MOSFET, there is produced a quantitative measure of the conductance of the element under test.

In general, for one-dimensional sensing channels other than the inversion channel of a MOSFET, time-dependent measurements of the conductance of such a sensing channel can be employed to produce a quantitative measure of the conductance of an element under test. The conductance measurement is independent of the particular sensing channel that is employed.

This method of measuring the electrical conductance of an element is insensitive to contact effects of the contacts that are connected to the element under test, i.e., the electrical conductance of the element can be determined for any contact resistance and for both Ohmic and blocking contact configurations, because application of a voltage between contacts on the element induces charge flow through the element by capacitive coupling between the contacts and the element, and then the sensing channel capacitively senses this charge flow in the element. As discussed below, the conductance measurement method can measure conductance as low as $10^{-25}$ S or smaller with application of a very low voltage, e.g., about 1 V, to the element under test. This measurement technique is applicable to any element or structure, e.g., thin solid films, for which electrical contact to the film can interfere with current measurements, and for materials and structures for which electrical conductance may be immeasurable with conventional techniques due to a very high electrical resistivity of the structure. The conductance measurement method thereby enables progress in the development of new materials, such as novel organic semiconductors and nanoscale materials, in which contact effects often limit efforts to electrically characterize and to understand material properties.

Figure 3:
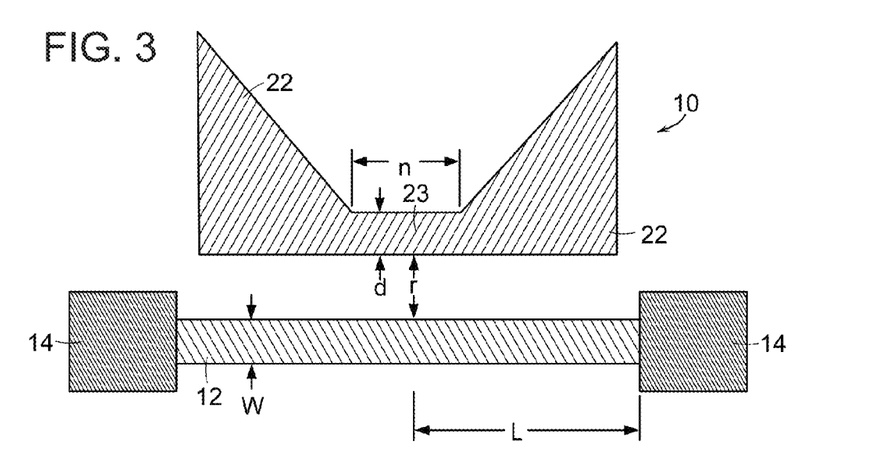
FIG. 3 is a schematic top-down view of conductance measurement system of FIG. 1, illustrating the geometric parameters of the system.

Referring to FIG. 3, there is shown a schematic top-down view of an example conductance measurement system configuration 10. The geometry of the system enables reliable conductance measurement by capacitive coupling in the manner just described. A MOSFET gate 22 can be provided as any suitable geometry, and preferably includes a tapering or narrowing to a narrowed constriction 23 having a constriction length, n, and a constriction width, d. The constriction length, n, is preferably as short as possible. The shorter the constriction length, n, the higher the sensitivity of the MOSFET measurement. To sense charge motion, a charge must move either closer to or further away from the narrowed constriction of the MOSFET gate. Thus, the shorter the length of the constriction, the easier it is to detect when a charge has moved further or closer to the location of the narrowed constriction. It is therefore preferred, in general, that the length, n, of the constriction, be as short as microfabrication processing will allow.

The gate constriction width, d, is preferably sufficiently narrow to be characterized as producing a one-dimensional inversion channel in operation, in that the inversion channel conductance is sensitive to individual charge fluctuations in the environment of the inversion channel. A constriction region width, d, of less than about 100 nm can be preferred for most applications to achieve one-dimensional MOSFET inversion channel operation for a silicon-based MOSFET.

The length of the narrowed constriction is substantially entirely disposed a distance, r, from the element for which a conductance measurement is desired. The midpoint of the narrowed gate region is preferably aligned with the midpoint of the element. It can also be preferred that the element be substantially parallel to the length of the constriction. The sensitivity of the inversion channel determines how far from the MOSFET gate constriction the element can be disposed from this parallel element while still enabling a conductance measurement of the element.

The distance, r, between the element and the inversion region of the MOSFET, as shown in FIG. 3, sets the level of capacitive coupling between the two. The typical change in conductance in a silicon-based MOSFET is approximately 1 μS to 2 μS when charge diffuses in the element, for a gate voltage of about 10 V and a MOSFET bias of about 5 mV, with the voltage on the element stepped by about 1 V. For these geometric and biasing parameters, the MOSFET can resolve a change in conductance that is as small as about 10 nS.

When the element under test electrically charges up due to application of a voltage across its contacts, a mirror electrical charge of the opposite polarity is induced in the substrate beneath the element. For this reason, the signal from the element under test decreases as the field from a line of dipoles, as $1/r^2$, where r is the distance from the element to the MOSFET, as shown in FIG. 3. For example, an increase in the distance, r, from 100 nm to 800 nm, causes the signal to decrease by a factor of 100, which is still easily measurable. Based on this, for example, given a 70 nm-wide MOSFET gate narrowed constriction, a gate voltage of 10 V, and a MOSFET bias of 5 mV, with a 1 V voltage step on the element under test, about 800 nm is the maximum preferable distance between the MOSFET gate narrowing constriction and the element under test. In other words, so long as the narrowing constriction of the MOSFET gate is disposed a distance, r, that is less than about 800 nm from an element under test, the MOSFET can sense charge diffusion in the element by capacitive coupling with the element.

Considering now how large the contact capacitance needs to be to charge an element sufficiently so that the MOSFET can sense the diffusion of charge in the film, given a MOSFET sensitivity in which the addition of a charge to a 100 $n^{m2}$ area of element that is 100 nm away from the MOSFET results in a change in conductance of 0.4 μS in the MOSFET, which is easily detectable, then the element needs to be charged by 1 electron per 100 $n^{m2}$ of element area. Given that $Q = C_{contact} V$, where Q is the total charge added to an element that can be considered two-dimensional, e.g., having a geometry of 200 nm wide×1 μm long and the voltage applied to the contact V=1 V, then the contact capacitance, $C_{contact}$, needs to be at least about $8^{e-19}$ farads. It is here assumed that the thickness of the element is less than the screening length of the element material, and is the reason for considering the element as two-dimensional.

Now considering requirements for distance between the midpoint of the element, which is preferably aligned with the midpoint of the MOSFET narrowed gate constriction, to the contact locations at the ends of the element, which distance is given in FIG. 3 as L, it is first noted that because the element is charged capacitively, it is preferred that the total length of the element exceed the screening length in the element; otherwise the element cannot be electrically charged. The so-called screening length refers to the screening of the electric field in the material by mobile charges, and specifies the distance over which such screening occurs. In other words, an electric field is felt only within a radius given by the screening length. Using the Thomas-Fermi approximation, the screening length is given in SI units as $(K \in_0 /e^2 D(E_F))^{1/2}$, where K is the static dielectric constant, $\in_0$ is the permittivity of free space, e is the electron charge, and $D(E_F)$ is the density of states at the Fermi energy for the material of the element under test. The screening length can vary from several nanometers to tens of nanometers, depending on the material of the element that is being measured. Second, the MOSFET senses the change in charge in the element as charge diffuses toward one of the contacts. For this reason, the distance, L, between the midpoint of the element and the narrowed gate constriction, where the MOSFET senses the charge, and either of the two contacts is preferably sufficiently long for the MOSFET to sense that there has been a change in charge at the midpoint of the element.

When the element becomes charged, an equal amount of opposite charge accumulates at the contacts. If the opposing charge is very nearby to the midpoint of the element, then the opposing charge will diminish the electric field that is established by the charged element. For this reason, the distance, L, between the midpoint of the element and the end preferably exceeds the screening length, and preferably exceeds the screening length by at least three times the screening length. The electric field established by the charge in the element decreases as $1/r$ as long as the distance, L, is several times the screening length. If the distance, L, is less than three times the screening length, then the field will diminish as $1/r^3$. It is therefore preferred that the contacts on the element under test be disposed a distance, L, that is at least 3× screening length for the material.

With these geometric considerations, the conductance measurement system 10 can be configured with a suitable sensing channel, such as a MOSFET device structure, in the vicinity of an element for which a conductance measurement is desired. For many applications, it can be convenient to fabricate a sensing channel, such as the MOSFET, with a process that also accommodates the fabrication of an element to be tested or the manipulation of an element into place near the site of the MOSFET. The MOSFET can be integrated directly in a system including the element to be tested. No particular MOSFET fabrication process is required and the element to be tested can be fabricated in situ with the MOSFET or transferred to the site of the MOSFET subsequent to fabrication in a different environment.

In one example process, the MOSFET is provided as an n-channel MOSFET and is fabricated by standard CMOS methods. Referring back to FIG. 1, the substrate 16 can here be provided as any suitable material for this process. For example, there can be employed a p-type silicon substrate that is doped with, e.g., boron, at a level of, e.g., about $3 \times 10^{15}$ cm$^{-3}$. An electrically insulating layer 18 is provided on the substrate as, e.g., a layer of nitride, oxide, or other material for enabling production of a MOSFET insulating region. In one example, a layer of $SiO_2$, having a thickness of, e.g., about 650 nm, is formed as a field oxide layer on the substrate. Wet thermal oxidation or other suitable process can be employed to produce this field oxide layer. The insulating layer of, e.g., $SiO_2$, is patterned and etched to define an active region of suitable area, e.g., of 350×x220 μm$^2$.

To produce n-type source and drain regions 24, 26, for the MOSFET, any suitable dopant, e.g., phosphorous, can be implanted in the substrate in two areas of the active region, with source and drain dimensions of, e.g., about 100×150 μm$^2$, and separated by a selected distance for the inversion channel, e.g., about 100 μm. For the gate oxide, a layer of silicon dioxide of a suitable thickness, e.g., about 100 nm thick, can be grown in the active region, e.g., via dry, thermal oxidation. This gate oxide layer is preferably relatively thick to ensure that the MOSFET gate does not screen the inversion layer from the nearby electrostatic fluctuations of the element under test.

To form the MOSFET gate, there can be employed any suitable electrically conducting material, e.g., polysilicon. In one example process of such, there can be deposited a suitable layer, e.g., about 80 nm, of n$^+$ polysilicon on top of the gate oxide. The polysilicon is deposited and patterned, e.g., with electron beam lithography, to define the narrowest constriction region of the gate with a thickness set by the geometric considerations given above, ≈60 nm in width. The structure is then annealed with a sufficient annealing process to activate dopant, e.g., annealing at about 900° C. for a duration of about one hour.

With this MOSFET construction, it is found that under some circumstances, the MOSFET design can result in parasitic surface charge leakage. The $SiO_2$ of the MOSFET typically includes some trapped electrical charge per unit area of oxide, $n_{ox}$. This trapped charge can include a number of distinct charge components, including, e.g., mobile ionic charge from alkali impurities or other defects, but the sign of the net charge is typically positive. For an n-channel MOSFET, this positive charge has the effect of lowering the threshold for inversion, and if there exists sufficient charge, there can be produced an inversion layer at the silicon-oxide interface even under conditions of no gate bias application, when the oxide charge is at least as large as the amount of charge in the depletion layer of the MOSFET in inversion, $n_{min}$.

Given the silicon substrate doping concentration of $3 \times 10^{15}$ cm$^{-3}$, the amount of charge in the depletion layer of the MOSFET in inversion is calculated to be $n_{min} \approx 1.5 \times 10^{11}$ cm$^{-2}$. This is not an unusual amount of trapped charge for $SiO_2$ grown under conventional conditions. Oxide charge is therefore expected to cause parasitic surface leakage for the MOSFET design. This leakage can be eliminated by applying a reverse bias to the substrate, $V_{sub} \approx -3$ V. This reverse bias produces a depletion region width, $L_D$, that is larger than the width of the inversion layer, $L_{inv}$, and therefore increases the charge in the MOSFET depletion layer in inversion, $n_{min}$. As a result, the parasitic conduction path is eliminated. For the MOSFET production described above, it can therefore be preferred to employ a substrate reverse bias to eliminate any surface leakage.

After completion of MOSFET fabrication, or formation of other suitable sensing channel, an element to be conductance-tested can be disposed at a selected distance from the sensing channel at which the two are capacitively coupled, based on the geometric considerations and biasing suggestions given above. Alternatively, the element to be tested can be positioned on a support structure and the MOSFET is subsequently produced at the structure at the requisite location. In either case, the element for conductance measurement can be provided as any suitable structure or composition, including, e.g., organic materials, biological molecules, chemical compositions, microelectronic structures, nanoscale objects, or other element.

One example class of elements to be conductance-tested consists of a layer of material. The conductance measurement method is particularly application to thin films of material for which the electrical resistivity can be too high to accommodate conventional resistance measurements. The material can be disposed on a substrate adjacent to the MOSFET or alternatively can be provided on a support structure on which the MOSFET is then fabricated. In one example process, the MOSFET is protected after fabrication and a strip of the material layer of interest is formed at a selected location in the vicinity of the MOSFET.

For example, a layer of polymethyl-methacrylate (PMMA) can be spun on the surface, over the MOSFET, and electron-beam lithography employed to define a trench in the PMMA that is the selected length and width, or other dimensions, of the material strip to be tested; a rectangular material strip is not required, but can be preferred based on the geometric considerations discussed above. The trench is a distance, r, from the MOSFET gate narrow constriction, that was determined based on the geometric considerations discussed above. Electrodes are first formed on the substrate, e.g., by a lift off photolithographic process. Electrodes can be formed of any suitable material or material combination, e.g., a 30 nm-thick layer of titanium with a 300 nm-thick layer of gold. The film of material to be tested can then be deposited by any convenient method, and patterned by lift off of the PMMA.

Figure 4A:
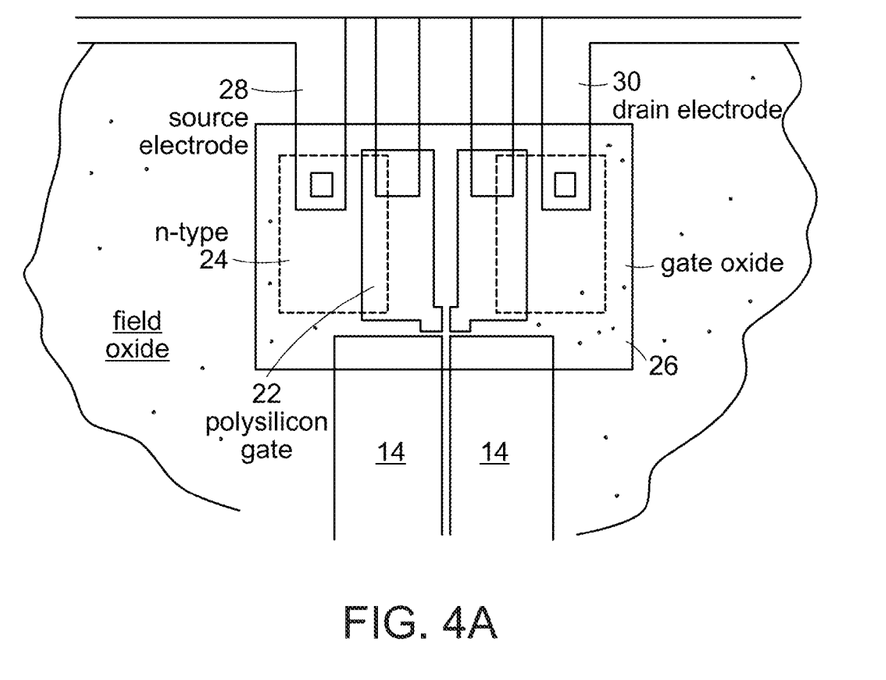
FIGS. 4A-4B are plan and side views, respectively, of an example fabrication construction of the conductance measurement system of FIG. 1.
Figure 4B:
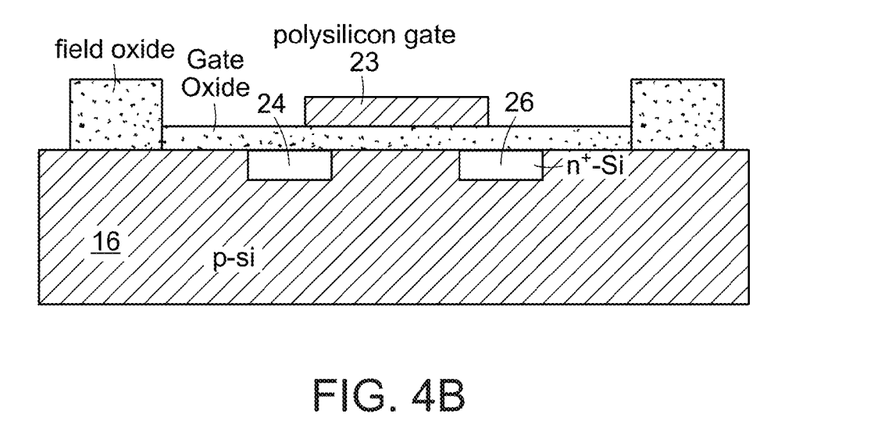

With this step, there is provided an element for which a conductance measurement is desired, spaced from the MOSFET and of a selected length that enable capacitive coupling between the element and the MOSFET. No particular process is required for producing an element to be tested, and three-dimensional structures and devices can be formed in addition to thin films. FIGS. 4A-4B are top down and side views of an example MOSFET microfabrication construction with a thin film for which a conductance measurement is to be conducted. In this construction, there is shown the source and drain electrodes 28, 30, making contact to n-type source and drain regions 24, 26, which the gate electrode 22 overlaps. Electrically-conductive contacts 14 are provided for connection with the thin film, which is located a distance from the gate.

Figure 5:
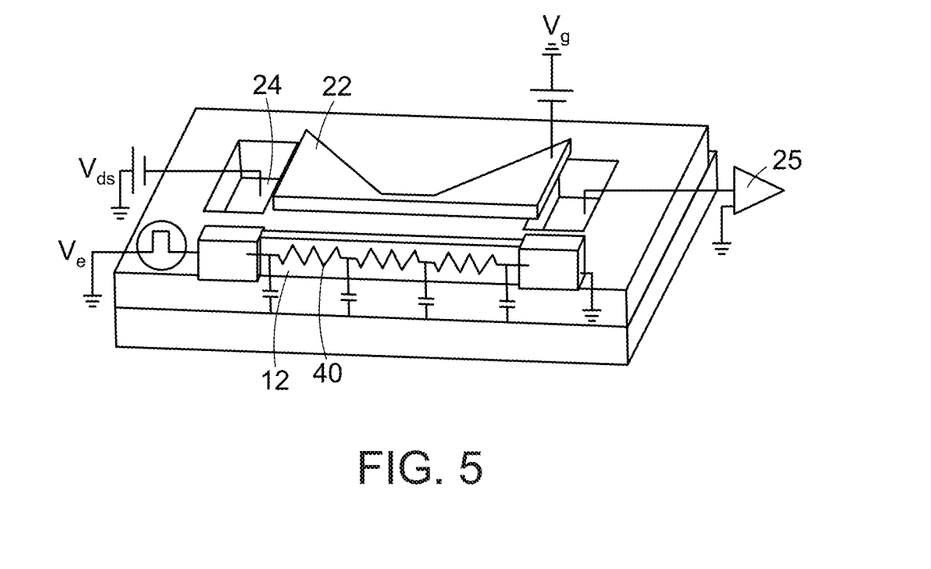
FIG. 5 is a perspective schematic view of the conductance measurement system of FIG. 1, including circuitry for operationally biasing the system, and including an R-C circuit model for analyzing the system operation.

With a selected element, such as a thin strip of material, in place at the site of the MOSFET, a conductance measurement can be carried out. Referring to FIG. 5, the sensor system is first electrically biased. A positive voltage is set at the gate of the MOSFET, e.g., $V_g > 6$ V, to ensure that the channel is in inversion. Then a voltage bias on the element, $V_e$, applied between the contacts that are connected to the element under test, is stepped so that charge flows in the element, and the conductance of the MOSFET is simultaneously measured as a function of time. To measure the conductance of the MOSFET, a source-drain voltage is applied, e.g., $V_{ds}=5$ mV, and the current in the MOSFET is measured. This conductance measurement can be performed using either an ac or a dc excitation.

Figure 6:
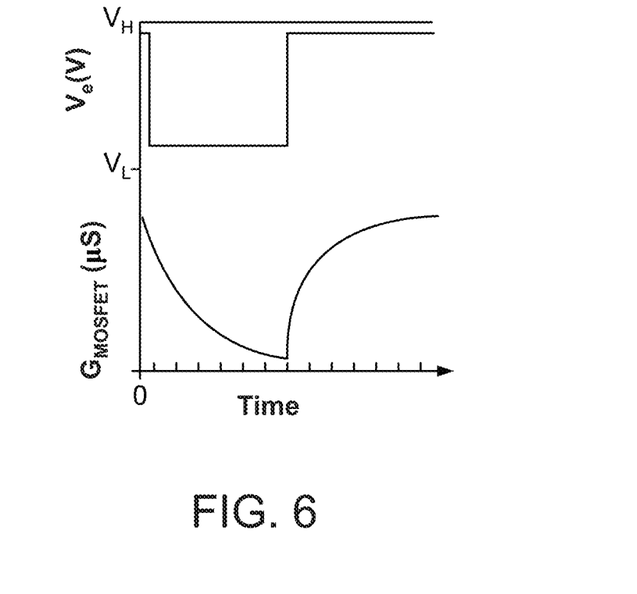
FIG. 6 is a plot of voltage applied across an element during a conductance measurement and the resulting MOSFET conductance.

Referring to the plots of FIG. 6, in one example measurement control scenario, at time t=0, the voltage, $V_e$, across the element under test is stepped from a starting, high voltage, $V_H$, to a lower voltage, $V_L$. The difference in voltage between $V_H$ and $V_L$ is preferably sufficient to generate charge flow though the element, but small enough to not alter the conductance of the element by the voltage application itself, and therefore can be particular to a given element under test. For example, a voltage step of about 0.5 V or about 1 V can be sufficient to generate charge flow through an element that is a layer of material. The starting high voltage, $V_H$, is selected based on the voltage for which conductance information is desired, and then a voltage step that is sufficient to generate charge diffusion in the element is imposed on the element.

Even if contact resistance limits the current in the element, capacitive coupling between the electrodes and the element causes positive charge in the element to flow toward the negatively-biased electrode. The n-channel MOSFET senses the decrease in positive charge in the vicinity of the narrow constriction of the gate, and the conductance of the MOSFET, $G_{MOSFET}$, decreases with time. The lower voltage, $V_L$, is maintained for a duration that is sufficient for the charge transient in the MOSFET to settle to a constant value. After the selected duration at the low voltage, the voltage across the element, $V_e$, is then stepped back to the high starting voltage, $V_H$. Here, positive charge flows away from the negatively-biased electrode and the conductance of the MOSFET increases with time as shown in FIG. 6. This response of the MOSFET to the charge flow in the element under test is henceforth referred to as the MOSFET charge transient.

The MOSFET charge transient is analyzed as follows to determine the conductance of the element under test. Referring to FIG. 5, the element under test 12 is modeled as a distributed RC network 40. When the element is subjected to a step voltage at one edge, charge diffuses through the element with a diffusion constant of $D=1/R_{sq}C$, where $R_{sq}$ is the resistance per square of the element and C is the capacitance per unit area of the element. In the device geometry shown in FIG. 5, the capacitance between the element and the underlying substrate is the dominate source of capacitance of the element. By solving the diffusion equation for this system, it is found that the charge per unit area, $\sigma(t)$, at any point along the element thereby varies with time according to:

$$\sigma(t) \approx \sigma_0 + A\exp(-\Gamma t), \text{ where } \Gamma = \pi^2 D/X, \quad (1)$$

and where X is the length of the element, D is the diffusion constant, and A is a constant that depends on the voltage applied across the element and the capacitance of the element. So long as the voltage step applied to the element is sufficiently small, e.g., less than about 1 V, the conductance of the MOSFET varies linearly with the charge in the element, and the MOSFET conductance as a function of time, $G_{MOSFET}(t)$, is given as:

$$G_{MOSFET}(t) \approx G_0 + B\exp(-\Gamma t), \text{ where } \Gamma = \pi^2/R_{sq}CX^2, \quad (2)$$

and B is a constant.

The conductance of the element under test, $G_E$, is then given as:

$$G_E = w/R_{sq}X, \quad (3),$$

where w and X are the width and length of the element, respectively, with X=2L as given in FIG. 3. From this expression, it is shown that the conductance of the element, $G_E$, can be derived from the charge transient of the MOSFET. In the example transient plot shown in FIG. 6, the transient profile is fit to this form, and a value for the parameter $\Gamma$, the rate of charge flow in the element, is given. From this, then, is determined the element conductance, $G_E$, and the resistance of the element, given as $R_E=1/G_E$.

Any number of biasing arrangements can be employed to characterize conductance dependence. For example, by changing the voltage difference between the element under test and the underlying substrate, the substrate can serve as a back gate and the conductance of the element can be measured as a function of gate voltage.

It is notable that the measurement of conductance of the element comes from the time-decay of the transient in the MOSFET, which is independent of the characteristics of the MOSFET as long as the transient signal is small enough that the conductance of the MOSFET versus gate voltage is linear and large enough to be measured above the noise of the MOSFET. For this reason, the measurement technique is insensitive to discrete changes in the conductance of the MOSFET due to, e.g., a change in temperature.

But the resistance of the MOSFET channel can be found, under certain circumstances, to oscillate between two discrete values. Specifically, a high resistance state can arise when an electron is trapped in the nearby silicon dioxide and a low resistance state can arise when the electron is released from the oxide trap. This charge trapping and release produces so-called random telegraph noise, and can occur when the gate voltage of the MOSFET is tuned such that a trap in the oxide, of trap energy, $E_T$, is resonant with the Fermi energy, $E_F$, in the MOSFET inversion channel. The resulting charge fluctuation within the MOSFET itself contributes noise to the measurement of charge outside the MOSFET, such as the charge flow through an adjacent element for which a conductance measurement is desired.

Figure 7:
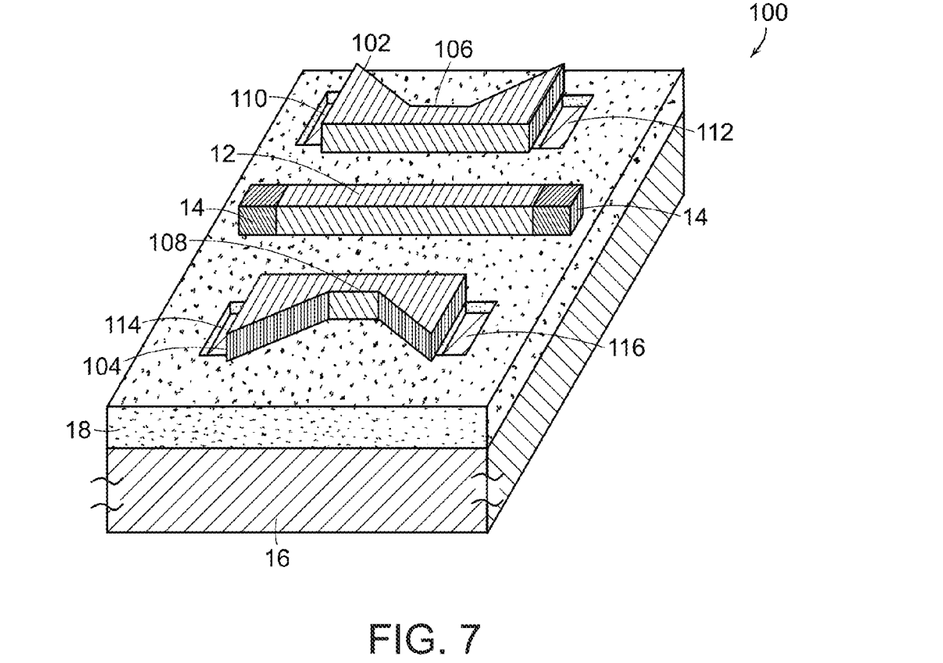
FIG. 7 is a perspective schematic view of a second example conductance measurement system.

Referring to FIG. 7, there can be employed a multi-MOSFET conductance measurement system 100 that enables the elimination of telegraph noise that is produced in each MOSFET, and that thereby enables an increase in sensitivity in the measurement of conductance of an element such as a thin film structure. As shown in FIG. 7, in a first example of such a system, a first MOSFET 102 and a second MOSFET 104 are configured on a support structure 16, such as a semiconductor substrate in the manner described above, e.g., with a layer of field oxide 18. An element under test 12 is arranged between the two MOSFETs, with the narrowing gate constriction region 106, 108, of each MOSFET set a selected distance, r, from the element 12, in the manner described above. Source and drain regions, 110, 112, and 114, 116, are provided for the two MOSFETs, and provided with electrical connections in the manner described above.

Each of the two MOSFETs is subject to charge fluctuations and resulting telegraph noise, but is insensitive to fluctuations in the neighboring MOSFET so long as the neighboring MOSFET is sufficiently far away. When charges fluctuate in the trap states of the silicon dioxide, giving rise to the telegraph noise, the trap states are typically 1-10 nm deep into the oxide relative to the inversion region of the MOSFET. This charge fluctuation is detectable by one MOSFET when the fluctuation occurs directly beneath the narrowed constriction in inversion region of that MOSFET. However, for a MOSFET that is at least about 100 nm away from the trap state, the signal from the fluctuation is too far to detect. With this geometry, the conductances of the two MOSFETs that arise from charge transport through an element under test are correlated but the noise in the two MOSFETs is uncorrelated. Therefore, with correlation analysis of the conductance signals from the two MOSFETs, a conductance measurement free of telegraph noise can be determined, with corresponding increased sensitivity.

In operation, each of the MOSFETs is biased in the manner described above, and the element under test is biased, with a voltage step applied to the element just as explained above. The charge transient signals produced by the two MOSFETs are then analyzed and compared to determine a single output conductance value based on the combined measurements.

Figure 8:
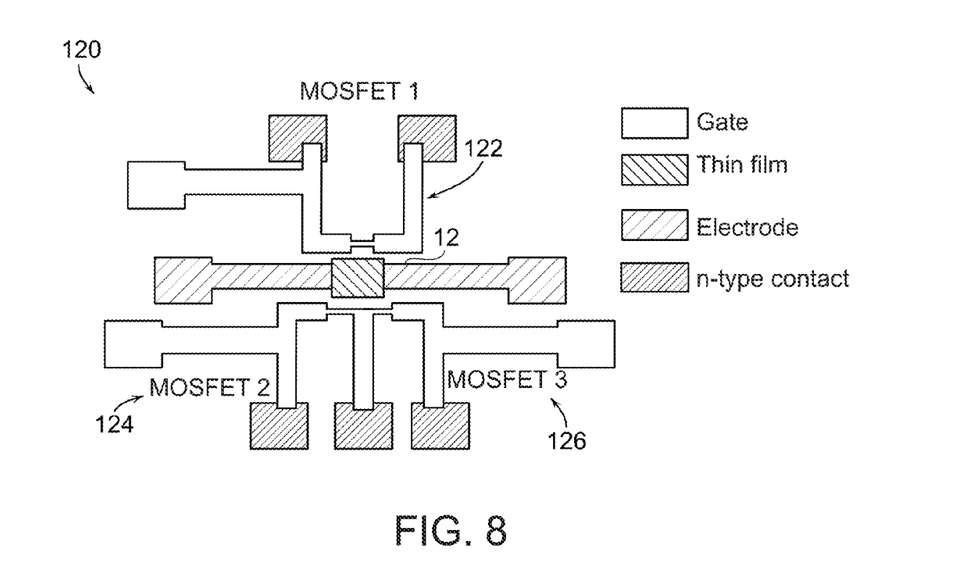
FIG. 8 is a schematic view of an electrical connection arrangement for a third example conductance measurement system.

The conductance measurement system is not limited to a two-MOSFET configuration. Referring to FIG. 8, there is shown a schematic view of the electrical contact arrangement for a conductance system 120 including a configuration of three MOSFETs 122, 124, 126, providing for the ability to detect the trajectory of a single electron in the element under test by means of a triangulated measurement.

With these example MOSFET configurations, it is demonstrated that a single or any selected number of MOSFETs can be employed for conductance testing of a selected element, device, structure, or material. Electrical conductance can be measured independent of contact effects, and exceedingly high electrical resistances can be measured nondestructively. For example, the conductance measurement system can be employed to electrically characterize materials such as high-dielectric constant materials, e.g., hafnium oxide, which is characterized by a very high resistivity. Further, the sensitivity of the conductance measurement system to single electron fluctuations enables the study of defects in materials such as high-dielectric constant materials that contain a high defect density. The understanding of charge dynamics in defect states by conductance studies can provide needed analysis for enabling commercial application of such materials. Thus, electrical characterization of high-resistance materials, and structures, and the study of their electronic defect states, can be achieved with the conductance measurement system.

The conductance measurement system can further be employed for measuring dynamic electrical processes in a material or structure. In such a study, the conductance of a material or structure can be monitored over time, to correlate time-dependent processes with the measured conductivity. For example, in photovoltaic materials, light is converted into electronic energy by the promotion of an electron from the valence band of the material to the conduction band, but recombination of charge at localized states in the energy gap between the conduction and valence bands can reduce the collection efficiency of such materials. When a photo-excited electron is suddenly localized at a recombination center, the conductance of the photovoltaic material changes. This conductance change can be sensed by the MOSFET of the conductance measurement system, thereby enabling a direct measurement of the dynamics of charge state at a recombination center in a photovoltaic material. The monitoring of conductance of an element under test over time, i.e., the monitoring of an element's conductance across several successive points in time, by way of MOSFET charge transient measurement across points in time, enables a time-dependent characterization of an element and the dynamics involved in electrical processes in the element.

In addition, the element, device, structure, or material to be tested by the conductance measurement system can in turn be selected and configured to be exploited for any in a wide range of sensing and control applications. For example, the element for which conductance is to be tested can be configured as a structure or material that is sensitive to some selected species in the environment of the element. In one example of such, the element under test can be provided as a chemically sensitive material, such as a polymer film, the electrical conductance of which is influenced by a particular molecule, e.g., nitrogen dioxide, in the environment. The conductance measurement system can thereby be employed as a chemical sensor by monitoring the conductance of a structure to make a determination of the influence of the environment on the structure and a corresponding determination of species type and concentration in the environment. The measurement system enables independent gating of the MOSFET and the structure, and enables integration into micro- and nano-electronic circuits.

These examples demonstrate the wide range of applications for measurement that can be achieved with the conductance measurement system. Organic, biological, solid state, and other structures and materials can be analyzed and dynamically studied to determine properties in an extremely convenient and direct process.

Example I

Characterization of Element with Blocking Contacts

A conductance measurement system like that shown in FIG. 1 and FIG. 2 was fabricated, with an n-channel silicon MOSFET fabricated on a p-type silicon substrate, employing conventional CMOS techniques, in the manner described above. The gate of the MOSFET was tapered to a narrowed constriction region having a width of about 60 nm at its most narrow point.

An element for conductance measurement was fabricated a distance of about 100 nm from the MOSFET gate narrowing constriction. The element was fabricated as a thin film of amorphous germanium, patterned as a strip having a width of about 200 nm and a thickness of about 50 nm. The amorphous germanium strip was centered with center of the narrow constriction of the gate. Formation of the film of amorphous germanium was completed after evaporation of gold electrodes for contact to the germanium element.

The gold electrodes were disposed about 1 µm apart, giving a distance from each gold electrode to the center of the gate constriction region of about 500 nm. This meets the screening length requirements given above for L greater than three times the screening length. The density of states of the amorphous germanium is $10^{20}$ eVcm$^3$, and the dielectric constant of amorphous germanium is 16, giving a screening length of about 30 nm using the expression given above. The amorphous germanium layer was formed by electron beam evaporation, with each end of the film overlapping one of the gold contacts. After fabrication, the system was maintained in a storage vessel with air and nitrogen gas, for a duration of at least two months.

Figure 9:
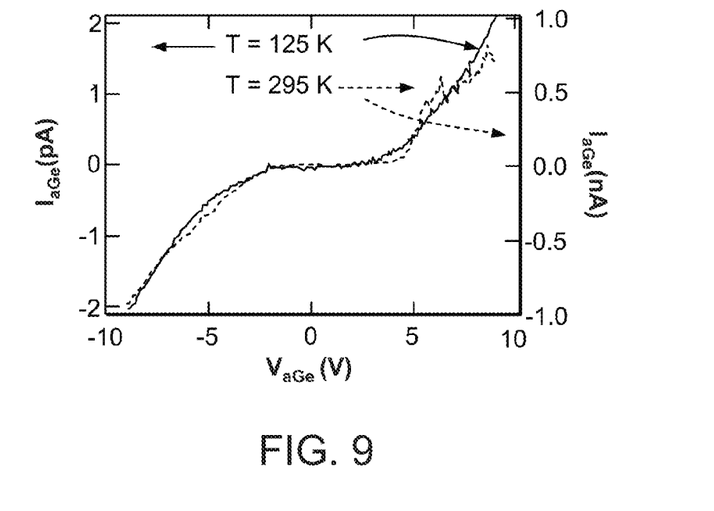
FIG. 9 is a plot of the measured IV characteristic of an amorphous germanium thin film for which a conductance measurement was conducted.

With this storage of the measurement system, it was found that an oxide had formed at the interface between the amorphous germanium film and the gold contacts, forming a blocking contact configuration that does not accommodate conventional conductance measurement techniques at reasonable voltages. To measure the conductance of the amorphous germanium film, a dc bias voltage, $V_{aGe}$, was applied between the two gold contacts, across the length of the amorphous germanium film, and the current, $I_{aGe}$, through the film was measured. This measurement was conducted at two temperatures, namely, 125 K and 295 K. FIG. 9 includes plots of the measured current as a function of voltage taken at the two temperatures.

As shown in FIG. 9, the IV characteristic is non-Ohmic. At an applied voltage of $|V_{aGe}|<5$ V, the current is immeasurable. The oxide interface between the gold electrodes and the amorphous germanium film introduced such a large contact resistance that the overall resistance of the system was dominated by the contact resistance at relatively low bias voltages. It was found that if a sufficiently high bias voltage, $|V_{aGe}|>5$ V, was applied, then the contact resistance decreased sufficiently that the conductance of the film could be measured with this conventional current measurement technique. This demonstrates that both contact-limited and Ohmic-contact regimes exist for the material, and that the conventional current measurement technique is viable only for the Ohmic-contact regime.

Example II

Characterization of MOSFET Conductance Sensor

Figure 10A:
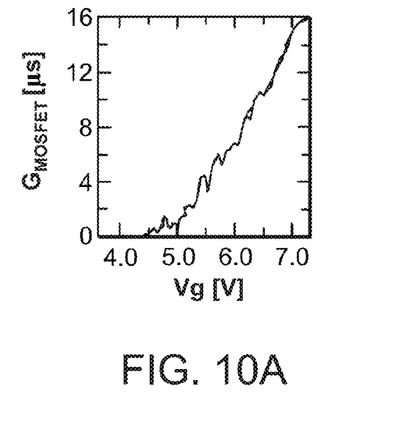
FIGS. 10A-10B are plots of measured conductance of an experimental MOSFET as a function of applied gate voltage and fluctuation of measured conductance of the MOSFET, respectively.

The MOSFET of Example I was characterized to measure its sensitivity to nearby electrostatic fluctuations. Maintaining the MOSFET at a temperature of about 4 K, the gate voltage was swept from 3.6 V to 7.2 V and then back down to 3.6 V, and the conductance measured. FIG. 10A is a plot of the measured MOSFET conductance as a function of applied gate voltage. The oscillations in the conductance that are clear in the plot were nearly identical in both directions of voltage application. This is typical of a one-dimensional inversion layer where random fluctuations in the local potential at the Si/SiO$_2$ interface cause oscillations in the conductance.

Figure 10B:
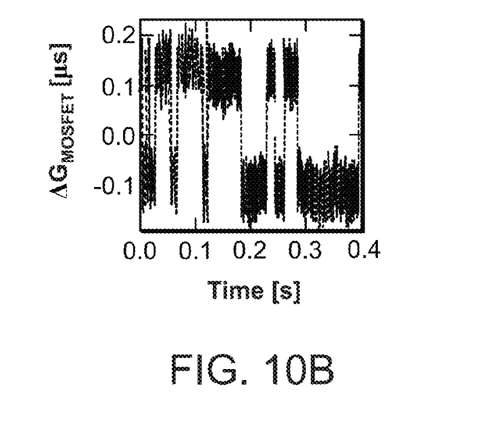

The gate voltage was then set to 8 V and the voltage between the source and drain, $V_{ds}$, was set to 1 mV, so that the channel was in inversion, and the dc current in the MOSFET was measured as a function of time at a temperature of 11 K. FIG. 10B is a plot of the MOSFET conductance fluctuation as a function of time. The prominent switching, or random telegraph noise, in this conductance is a result of a single electron being captured and emitted from a trap state in the silicon dioxide nearby the narrow constriction in the MOSFET channel, as explained above. The conductance of the MOSFET decreases when an electron is trapped nearby, and then increases when the electron is released. Although this is a noise characteristic of the MOSFET, it demonstrates that the MOSFET can sense the fluctuation of a single electron, and verifies the sensitivity of the MOSFET conductance to variation in the local electric potential, confirming the MOSFET capability as a charge sensor. It is this capability that enables the MOSFET to sense charge diffusion in a nearby element even when the contacts to the element are blocking.

Example III

Conductance Measurement

A conductance measurement of the amorphous germanium film of Example I was carried out with the MOSFET of Example I, with the geometric arrangement given. The biasing arrangement of FIG. 5 was employed. The voltage between the ends of the amorphous germanium film, $V_e$, as shown in FIG. 5, was stepped, so that charge flowed in the film, and simultaneously the conductance of the MOSFET was measured as a function of time. A positive voltage was maintained on the gate of the MOSFET, $V_g>6V$, to ensure that the channel was in inversion. A source-drain voltage, $V_{ds}$, of 5 mV was set at one of the source or the drain contact, with current flow measured at the other of the source or the drain contact, using a Femto 400 kHz bandwidth amplifier 25 in FIG. 5. The source-drain voltage was ac, obtained with a transformer. The output of the current amplifier was monitored with a Stanford Research 830 lock-in amplifier.

The amplifiers, as well as voltage dividers and filters for the source drain voltage, were mounted no more than a few feet away from coaxial connections at the top of a flow cryostat temperature control in order to minimize the size of the measurement circuit loop, thereby minimizing the noise and reducing the shunt capacitance at the current amplifier input. The voltage was supplied and monitored using an NI 6703/6251 output/input voltage card, divided and filtered as just given. The output of the current amplifier was further amplified and filtered with an Ithaco 1201 voltage preamplifier, and fed into a high speed voltage card, NI 6110, which can read in time series with a minimum step of 200 ns.

At time t=0, the voltage between the ends of the amorphous germanium film, $V_e$, was stepped from −0.5 V to −1

Figure 11A:
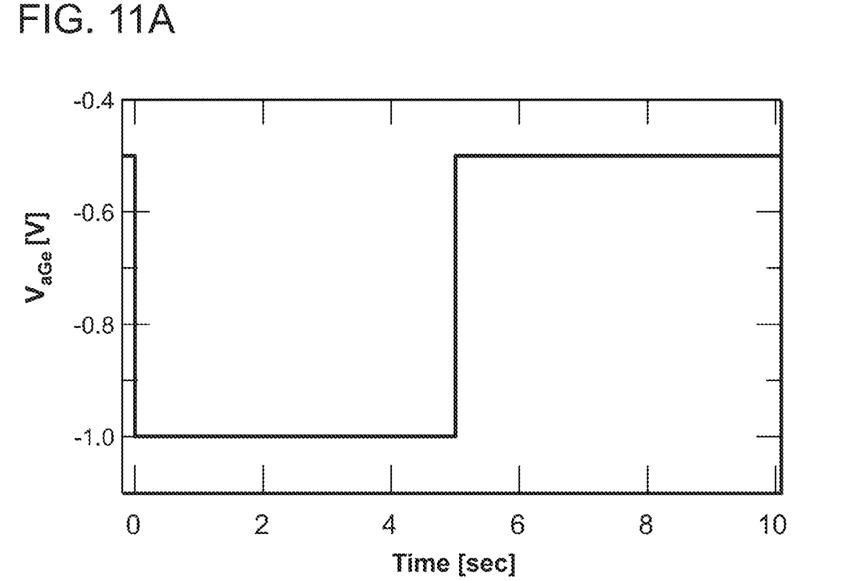
FIGS. 11A-11B are plots of the voltage, $V_{aGe}$, applied across an amorphous germanium film, at temperatures of 44 K and 54 K, and the measured conductance of the MOSFET as a function of time during the application of voltage across the germanium film, at each of the two temperatures, respectively.

V. After 5 s, the voltage between the ends of the amorphous germanium film, $V_e$, was stepped back to −0.5 V. This experiment was conducted at two temperatures, namely, 44 K and 54 K. FIG. 11A is a plot of the voltage, $V_e$, of the germanium film, given in the plot as $V_{aGe}$, and FIG. 11B is a plot of the measured conductance of the MOSFET as a function of time during the application of voltage across the germanium film, at each of the two temperatures.

Figure 12A:
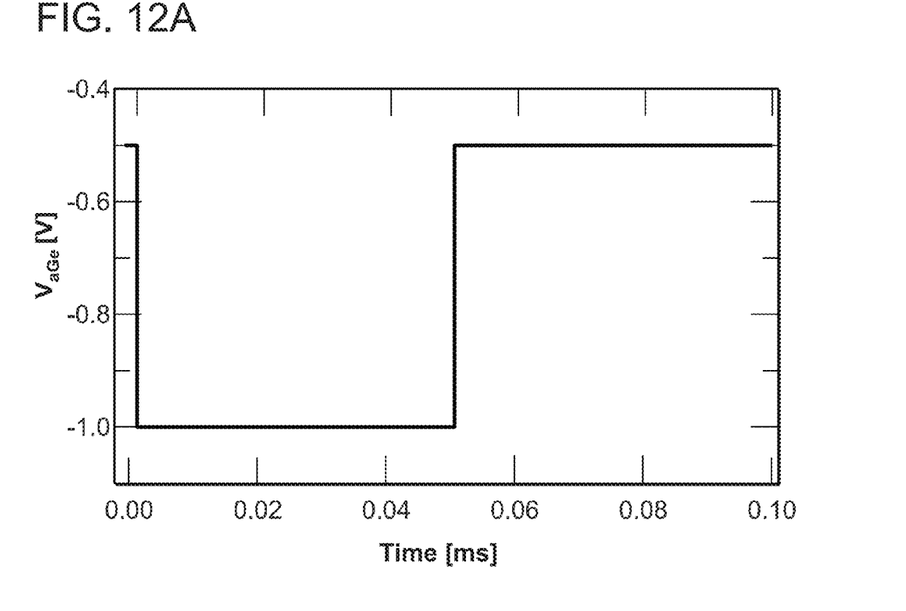
FIGS. 12A-12B are plots of the voltage, $V_{aGe}$, applied across an amorphous germanium film, at temperatures of 68 K, 77 K, and 90K, and the measured conductance of the MOSFET as a function of time during the application of voltage across the germanium film, at each of the three temperatures, respectively.
Figure 12B:
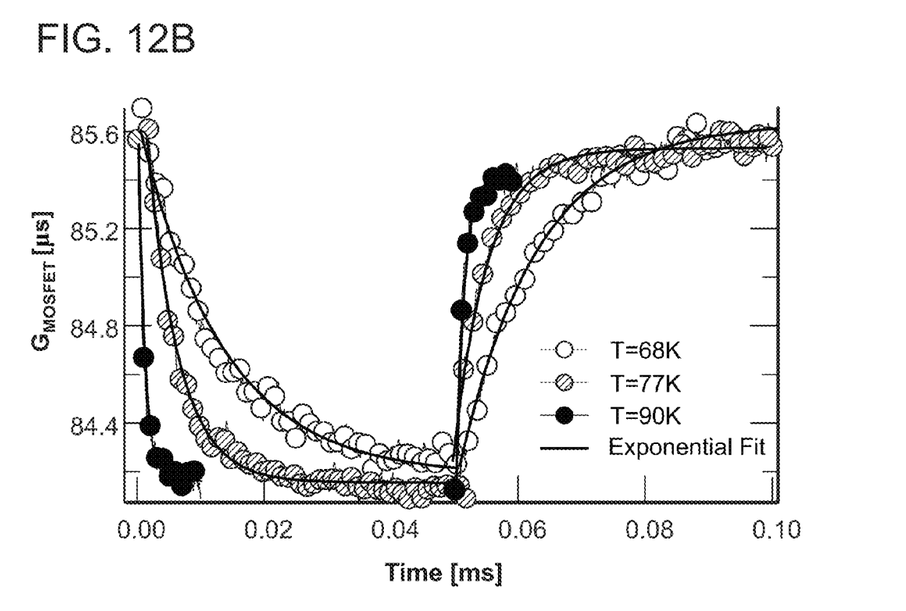

This experiment was conducted three additional times at temperatures of 68 K, 77 K, and 90K. FIG. 12A is a plot of the voltage, $V_e$, of the germanium film, indicated in the plot as $V_{aGe}$, and FIG. 12B is a plot of the measured conductance of the MOSFET as a function of time during the application of voltage across the germanium film, at each of the three temperatures. For these three experiments, the voltage between the ends of the amorphous germanium film, $V_e$, was stepped from −0.5 V to −1 V at time t=0 and then after 5 ms, the voltage was stepped back to −0.5 V.

Figure 11B:
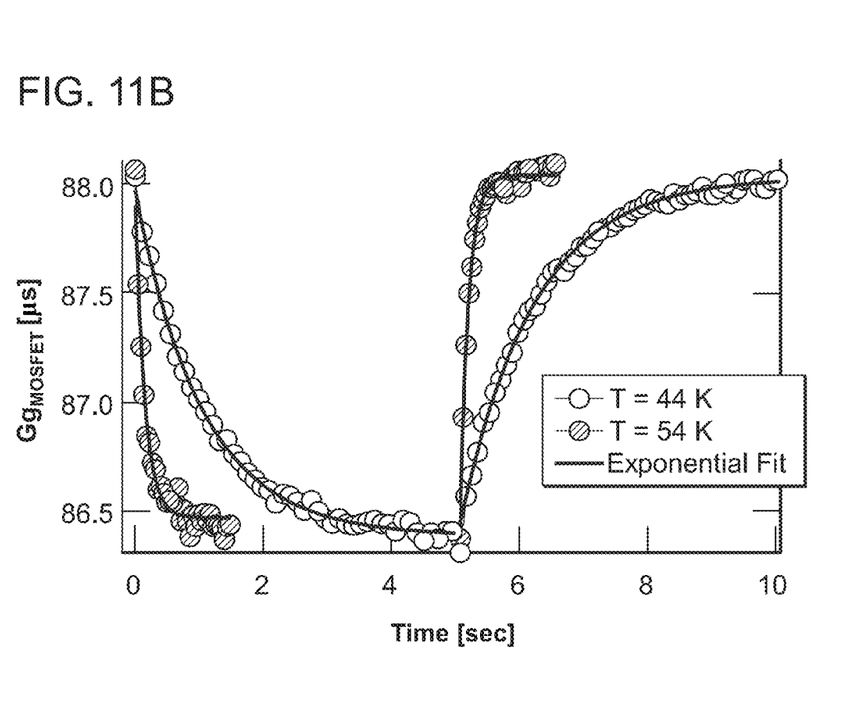

Employing the analysis given above, the charge transient plots of FIGS. 11B and 12B were fit to the form of Expression (3) above, and the parameter Γ was extracted from the data. This enabled a determination of the rate of charge flow in the germanium film, and hence the conductance of the germanium film. Table I below presents the conductance values resulting from the experimental measurements of FIGS. 11B and 12B.

TABLE 1

| Temperature | Germanium Conductance |
| --- | --- |
| 44 K | $1.3 \times 10^{-17}$ |
| 54 K | $9.4 \times 10^{-17}$ |
| 68 K | $1 \times e^{-15}$ |
| 77 K | $5 \times e^{-14}$ |
| 90 K | $1 \times e^{-14}$ |

Example IV

Conductance Measurements for Blocking and Non-Blocking Regimes

Conductance measurements of the amorphous germanium film of Example I were carried out with the MOSFET of Example I, with the geometric arrangement given. The biasing arrangement of FIG. 5 was employed with the biases of Example III. In a first set of measurements, the voltage between the ends of the amorphous germanium film, $V_e$, as shown in FIG. 5, was stepped from −0.5 V to −1 V and stepped back, for temperatures between 30 K and 125 K. In this biasing regime, the contacts limit the dc current flow. In a second set of measurements, the voltage between the ends of the amorphous germanium film, $V_e$, as shown in FIG. 5, was stepped from −4.5 V to −05.5 V and stepped back, for temperatures between 18 K and 125 K. In this biasing regime, with a voltage greater than 5 V, the contacts are not blocking. With the measurements as a function of temperature, the MOSFET was operated in a regime in which the MOSFET conductance was thermally activated.

Figure 13:
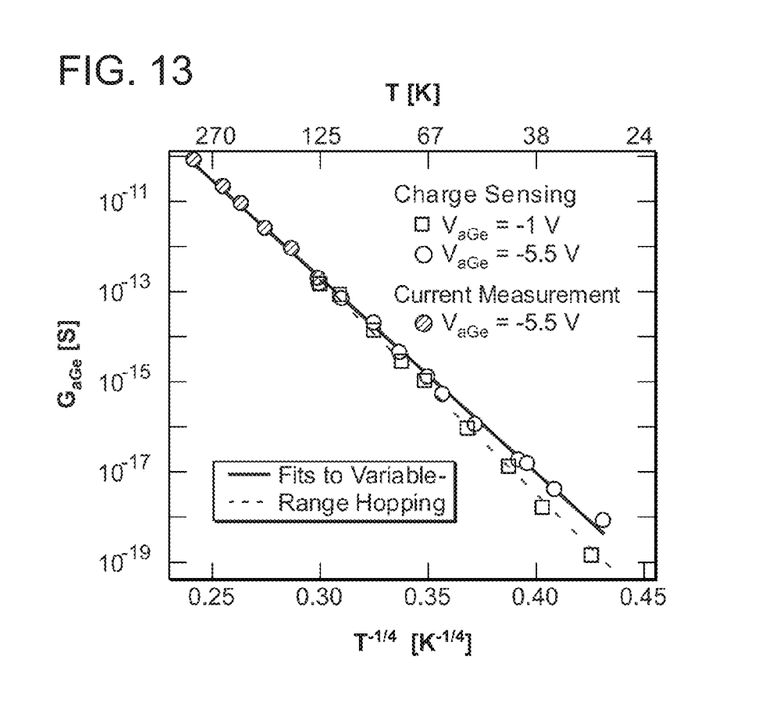
FIG. 13 provides plots of amorphous germanium film conductance, $G_{aGe}$, determined based on measured MOSFET charge transient, as a function of temperature, for a voltage, $V_{aGe}$, applied across an amorphous germanium film, of −1 V, −5.5 V, and −5.5 V.

For each of the two biasing regimes, the charge transient of the MOSFET was measured and the conductance of the amorphous germanium film, $G_{aGe}$, was determined across the temperature ranges. At temperatures ≥125 K, with a germanium film bias, $V_e$=−5.5 V, the conductance of the amorphous germanium film was determined by a conventional measurement of electrical current, $I_{aGe}$, through the film. FIG. 13 is a plot of the conductance of the amorphous germanium film as a function of temperature, as determined by MOSFET charge transient measurements and the direct conductance measurement.

At 125 K, the amorphous germanium film conductance was determined both by conventional current measurement and by derivation from MOSFET charge transient measurement. As shown in the plot, the resulting two conductance values agree within a factor of 1.3. This agreement confirms the validity of conductance determination based on a charge transient measurement.

In amorphous germanium, charge transport is dominated by hopping between localized states distributed in energy about the Fermi energy. At relatively high temperatures, hopping is expected to occur between nearest neighbor sites with an activation energy given by the distribution in nearest-neighbor site energies. But as the temperature is decreased, electrons do not typically hop between nearest neighbor sites, and instead, electrons tunnel to sites that are further away but closer in energy, via phonon-assisted tunneling. This is known as variable-range hopping, and the electrical conductance, G, associated with this hopping is given as $G = G_0 \exp(-T^*/T)^{1/4}$.

In FIG. 13, the conductance values for $V_e$=−5.5 V were fit to this model, as shown with a solid line. This fit set the parameter $T^* = 9.8 \times 10^7$ K. This value is in agreement with previous measurements for amorphous silicon.

Knowing that electrical transport in the Ohmic regime is described by variable-range hopping, the measured amorphous germanium conductance in the contact-limited regime in which the amorphous germanium bias, $V_e$, was set at −1 V, was also fit to this model, as shown in FIG. 13 by a dashed line. When this fit was extrapolated to temperatures greater than 125 K, it was found that the amorphous germanium film conductance, $G_{aGe}$, should be $G_{aGe} \geq 10^{13}$ and the current at these high temperatures should be easily measurable, e.g., >100 fA. The fact that it is not is consistent with the experimental finding here that the contacts limit the dc current.

Example V

Conductance Measurements as a Function of Electric Field

Conductance measurements of the amorphous germanium film of Example I were carried out with the MOSFET of Example I, with the geometric arrangement given. The biasing arrangement of FIG. 5 was employed with the biases of Example III. To conduct the measurements, a static electric field was applied across the amorphous germanium film, with one electrode held at ground potential and the other electrode held at a negative voltage value. This negative voltage level was then stepped by an additional −0.5 V and the charge transient of the MOSFET was measured. For example, to measure the conductance, $G_{aGe}$, at an applied bias voltage of $V_{aGe}$=−10 V, there was applied a fixed voltage $V_{aGe}$=−9.5 V and the voltage was rapidly stepped to −10 V. To accomplish the rapid voltage step, the output of a NI-6110 voltage cards combined with a Yokagaw 7651 voltage source with a ±30 V range. This enabled the addition of small high-speed voltage pulses to the large offset. To obtain high-speed measurements, the voltage was supplied and monitored using NI 6703/6251 output/input voltage card. These conductance measurements were conducted at a temperature of 33 K and at a temperature of 58 K.

Figure 14:
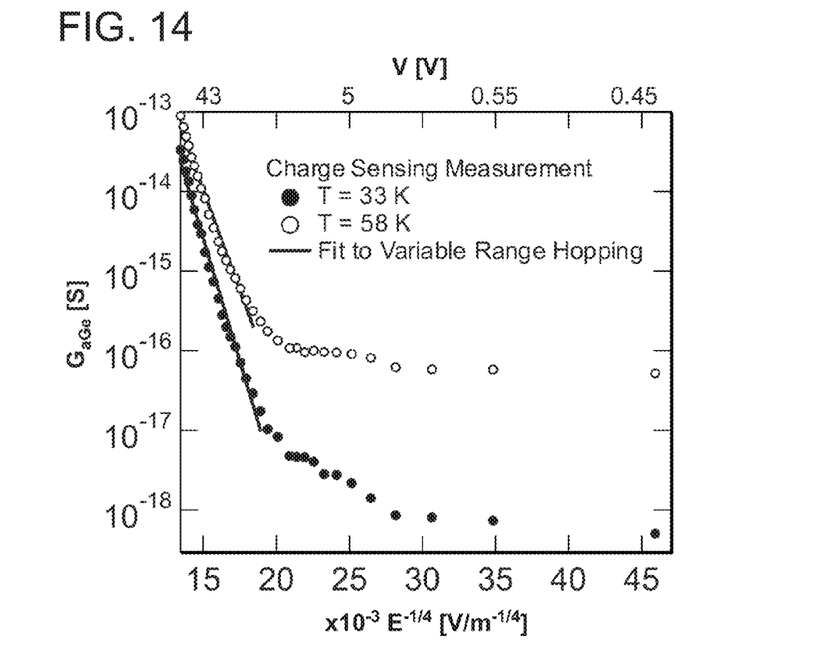
FIG. 14 provides plots of amorphous germanium film conductance, $G_{aGe}$, determined based on measured MOSFET charge transient, as a function of electric field, for the temperatures of 33 K and 58 K.

FIG. 14 provides plots of the amorphous germanium film conductance, $G_{aGe}$, that was determined based on the measured MOSFET charge transient, as a function of electric field, for the two temperatures under test. In the model of variable-range electron hopping discussed in Example IV above, given a sufficiently strong electric field, all electronic sites along the field direction will be lower in energy than previous sites along the field direction. Therefore, phonons are emitted as charges hop along the field, and the charge hopping is temperature-independent. In this regime, the conductance, G, is expected to follow a relation $G=G_0 \exp(-E^*/E)^{1/4}$. The data from the high-field regime of the measured conductance was fit to this expression, providing a value of $E^* \approx 7.7 \times 10^{12}$. This value of $E^*$ was employed with the value for $T^*$, determined in Example IV above, to determine the density of states, D, and Fermi energy, $E_F$, of the amorphous germanium film. These values can be determined with relations for $T^*$ and $E^*$, where $T^*=16/k_B D(E_F)a$ and $E^* \approx 16/eD(E_F)a^4$ where a is the localization length, $k_B$ is the Boltzmann constant, and e is the electron charge. Using the values obtained, it was determined that for the amorphous germanium film, the density of states at the Fermi energy, $D(E_F)=1.6 \times 10^{18}$ eV$^{-1}$ cm$^{-3}$, and the localization length, a≈1 nm. These experimental values are consistent with those previously reported for amorphous germanium with $D(E_F)=1.5 \times 10^{18}$ eV$^{-1}$ cm$^{-3}$, and a=1 nm.

For variable-range charge hopping, the temperature determines the typical distance a charge hops, r(T), and the width of the energy band about the Fermi energy in which a charge can hop, $\Delta\in(T)$. Variable-range hopping in a strong electric field, described by $G=G_0 \exp(-E^*/E)^{1/4}$, as given above, emerges when eEr(T), the decrease in potential energy over a hopping distance r(T) caused by the field E, is comparable to $\Delta\in(T)$. The critical field, $E_C$, required for a transition into this regime is given by $eE_C r(T) \approx \Delta\in(T)$, or $E_C \approx k_B T/ea$. From the data plotted in FIG. 13 for measurements at T=58 K, the onset of the strong-field regime occurs at a critical field of $E_C \approx 6.1 \times 10^6$ V/m, given a localization length of a≈0.8 nm, comparable to ≈1 nm determined by the expressions above. With this successful extraction of the density of states and localization length from the measurements of these examples, it is demonstrated that the measurement technique accurately characterizes the electronic properties of an element being tested.

Example VI

Characterization of Current Noise in Conductance Measurements

The conductance measurement system employed in the Examples above was analyzed for sources of current noise. In this analysis, the system was modified by replacing the sensing MOSFET with an 80 kΩ resistor, cooled to 4.2 K to eliminate Johnson noise. The current was monitored as a function of time, and the time series was digitally fast Fourier transformed to obtain the noise spectrum. For a frequency, f, <1 kHz, the current noise was measured to be approximately constant at ≈120 fA/Hz, with a few spikes at various frequencies, e.g., about 60 Hz, caused by coherent noise sources. At higher frequencies, e.g., f≈30 kHz, the noise was found to grow quadratically, due to current noise, $i_n$, and voltage noise, $v_n$, in the current amplifier. Given an RC circuit model for noise in a current amplifier, and estimating the capacitance, C, from the cables between the resistor and the current amplifier, it was determined that the current noise, $i_n \approx 70$ fAHz$^{1/2}$ and the voltage noise, $v_n \approx 7$ nV/Hz$^{1/2}$, in agreement with manufacturer specifications. As explained above, to minimize shunt capacitance, the current amplifier was mounted very close to the cryostat to reduce the current noise at higher frequencies.

With these examples and the description above, it is demonstrated that the conductance measurement system is applicable to any element or structure, e.g., thin solid films, for which electrical contact to the film can interfere with current measurements, and for materials and structures for which electrical conductance may be immeasurable with conventional techniques due to a very high electrical resistivity of the structure. The conductance measurement method and system thereby enable progress in the development of new materials, such as novel organic semiconductors and nanoscale materials, in which contact effects often limit efforts to electrically characterize and to understand material properties.

It is recognized that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. An electrical conductance measurement system comprising:
   a field effect transistor including an electrically-conducting gate that is disposed on an electrically-insulating surface of a substrate and that includes a narrowed gate region having a width corresponding to a one-dimensional inversion channel, the gate being connected to a voltage source bias providing a one-dimensional inversion channel in the substrate under the narrowed gate region, the transistor further including a source and a drain that are together in a circuit connected to measure electrical current through the inversion channel; and
   an electrically-conductive element disposed on the electrically-insulating surface of the substrate at a location at which the element is capacitively coupled to the transistor, with a midpoint of the element aligned with about a midpoint of the narrowed gate region, the element being connected to a first electrically-conductive contact pad and a second electrically-conductive contact pad that are together in a circuit connected to apply a changing voltage across the element, each of the first and second electrically-conductive contact pads being laterally spaced from the midpoint of the element by a distance of at least about three times a screening length of the element, with the screening length given in SI units as $(K\in_0/e^2 D(E_F))^{1/2}$, where K is the static dielectric constant, $\in_0$ is the permittivity of free space, e is the electron charge, and $D(E_F)$ is the density of states at the Fermi energy for the element.

2. The electrical conductance measurement system of claim 1 wherein the element is spaced from the narrowed gate region by a distance of less than about 800 nm.

3. The electrical conductance measurement system of claim 1 wherein the narrowed gate region width is less than about 100 nm.

4. The electrical conductance measurement system of claim 1 wherein the source and drain each comprise a semiconducting dopant region in the substrate.

5. The electrical conductance measurement system of claim 1 wherein the substrate comprises silicon.

6. The electrical conductance measurement system of claim 1 wherein the element comprises a semiconducting material.

7. The electrical conductance measurement system of claim 1 wherein the field effect transistor comprises an n-type metal-oxide-semiconductor field effect transistor.

8. The electrical conductance measurement system of claim 1 wherein the substrate is connected to a voltage source bias providing a reverse bias voltage to the substrate.

9. The electrical conductance measurement system of claim 1 wherein the electrically-insulating surface of the substrate comprises a layer of oxide.

10. The electrical conductance measurement system of claim 1 wherein the source and drain are connected in a circuit with a current amplifier.

11. The electrical conductance measurement system of claim 1 wherein at least one of the first and second electrically-conductive contact pads is characterized as being electrically-blocking.

12. The electrical conductance measurement system of claim 1 further comprising a second field effect transistor, the second field effect transistor including an electrically-conducting gate that is disposed on the electrically-insulating surface of a substrate and that includes a narrowed gate region having a width corresponding to a one-dimensional inversion channel, the gate of the second transistor being connected to a voltage source bias providing a one-dimensional inversion channel in the substrate under the gate of the second transistor, the second transistor further including a source and a drain that are together in a circuit connected to measure electrical current through the inversion channel of the second transistor; and wherein the electrically-conductive element is disposed on the electrically-insulating surface of the substrate at a location at which the element is capacitively coupled to the inversion channel of the second transistor.

13. The electrical conductance measurement system of claim 12 wherein the element is spaced from the narrowed gate region of the second transistor by a distance of less than about 800 nm.

* * * * *